(12) United States Patent
Jacobsen et al.

(10) Patent No.: US 6,224,572 B1
(45) Date of Patent: *May 1, 2001

(54) PISTON-ACTUATED ATTACHABLE TOPICAL FLUID DELIVERY SYSTEM

(75) Inventors: Stephen C. Jacobsen; Clark C. Davis, both of Salt Lake City, UT (US)

(73) Assignee: Sarcos L.C., Salt Lake City, UT (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/434,463

(22) Filed: May 4, 1995

(51) Int. Cl.[7] .................................................. A61M 5/00
(52) U.S. Cl. ........................... 604/181; 604/207; 604/186
(58) Field of Search ..................................... 604/181, 131, 604/134, 136, 139, 143, 146, 154, 156, 157, 186, 191, 201, 207, 213, 232, 71, 195, 196, 31, 33, 503–505

(56) References Cited

U.S. PATENT DOCUMENTS

| | | |
|---|---|---|
| 247,360 | 9/1881 | Jay . |
| 2,750,746 | 6/1956 | Brannen . |
| 2,766,701 | 10/1956 | Giraudeau . |
| 3,019,739 | 2/1962 | Prosser . |
| 3,353,537 | * 11/1967 | Knox et al. . |
| 3,509,890 | 5/1970 | Phillips . |
| 3,527,216 | * 9/1970 | Snyder ................................. 604/198 |
| 3,677,246 | * 7/1972 | Stein . |
| 3,731,679 | 5/1973 | Wilhelmson et al. . |
| 3,742,822 | 7/1973 | Talbert . |
| 4,042,248 | 8/1977 | Williamitis . |
| 4,074,694 | 2/1978 | Lee . |
| 4,280,741 | 7/1981 | Stoll . |
| 4,384,511 | 5/1983 | Mefferd . |
| 4,437,821 | 3/1984 | Ogawa . |
| 4,637,295 | 1/1987 | Powers et al. . |
| 4,909,783 | 3/1990 | Morrison . |
| 5,049,125 | * 9/1991 | Accaries et al. ........................ 604/71 |
| 5,144,882 | 9/1992 | Weissgerber . |
| 5,256,142 | * 10/1993 | Colvecchio ............................ 604/68 |
| 5,358,489 | * 10/1994 | Wyrick .................................. 604/136 |
| 5,380,279 | * 1/1995 | Schmidt ................................ 604/143 |

FOREIGN PATENT DOCUMENTS

| | | |
|---|---|---|
| 0272530A2 | 6/1988 | (EP) . |
| 0624379A1 | 11/1994 | (EP) . |
| 0654278A2 | 5/1995 | (EP) . |
| 0709573A1 | 5/1996 | (EP) . |
| 2077367A | 12/1981 | (GB) . |
| WO 81/01445 | 5/1981 | (WO) . |

* cited by examiner

Primary Examiner—Sharon Kennedy
(74) Attorney, Agent, or Firm—Thorpe, North & Western, LLC

(57) ABSTRACT

A fluid delivery device for delivering fluid from a fluid reservoir to a patient. The device includes an inlet channel in communication with a fluid reservoir and a dosing chamber, and an outlet channel disposed in communication with the dosing chamber. A reciprocating dosing actuator is moveable in a reciprocating motion between first and second positions for alternately (i) transporting a dose of fluid conveyed by the inlet channel into the intermediate dosing chamber, and (ii) ejecting the dose from the dosing chamber through the outlet channel to the patient, respectively.

30 Claims, 4 Drawing Sheets

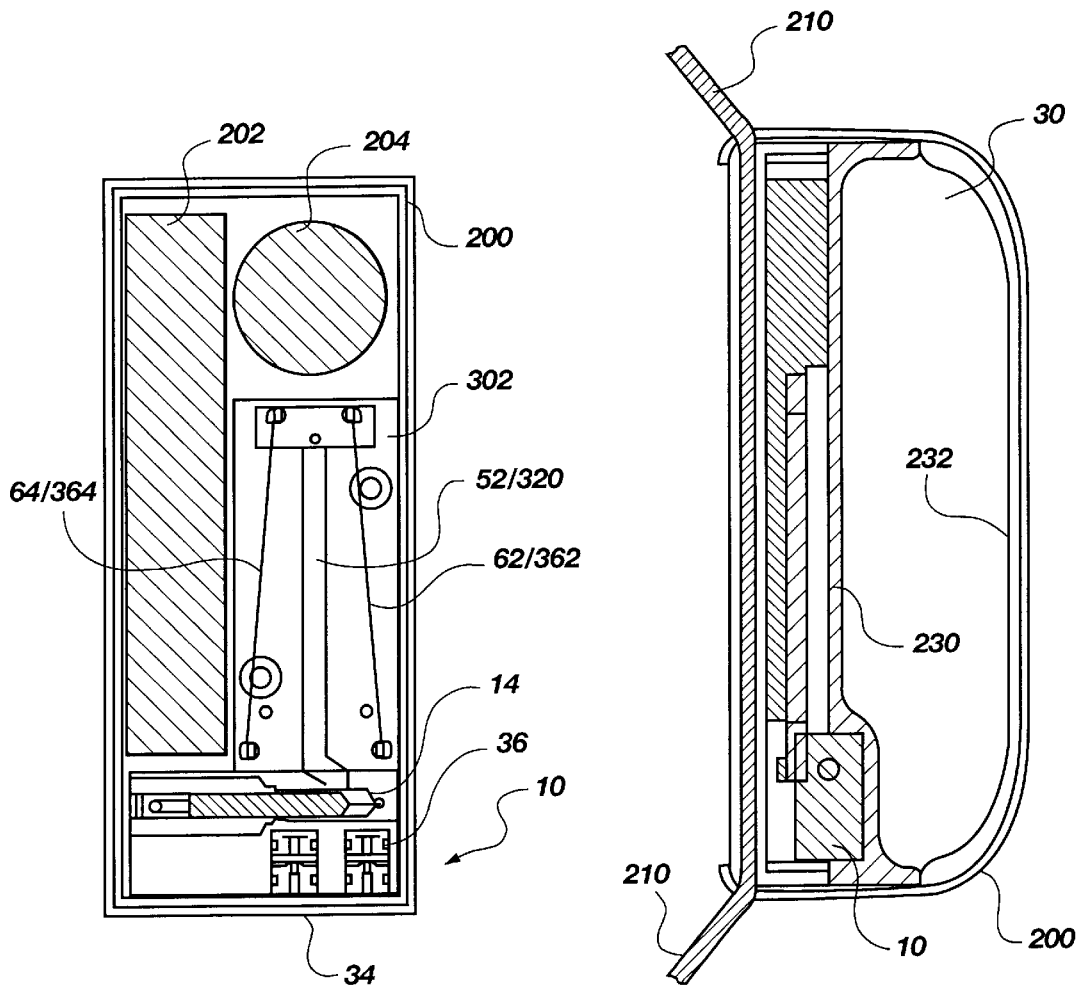
Fig. 5
Fig. 5B
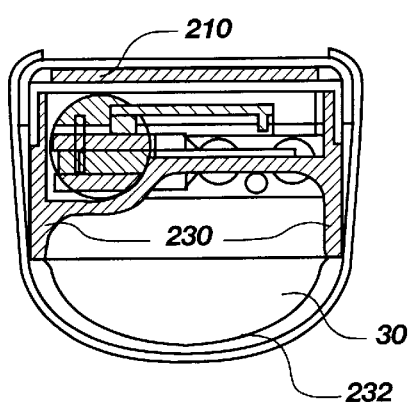
Fig. 5A

PISTON-ACTUATED ATTACHABLE TOPICAL FLUID DELIVERY SYSTEM

BACKGROUND OF THE INVENTION

1. The Field of the Invention.

The present invention relates generally to fluid delivery systems, and more particularly to lightweight, miniaturized fluid transport systems suitable for a variety of uses including topical and intravenous fluid delivery.

2. The Background Art.

The administration of fluids to patients is a well-known medical procedure for, among other things, administering life sustaining nutrients to patients whose digestive tracts are unable to function normally due to illness or injury, administering antibiotics to treat a variety of serious infections, administering analgesic drugs to patients suffering from acute or chronic pain, administering chemotherapy drugs to treat patients suffering from cancer, etc.

The intravenous administration of drugs frequently involves the standard syringe and needle. This simple method is not conducive to a progressive and systematic delivery of multiple doses of fluid over a longer time period. It is known to meet such needs with the use of an IV pump connected or built into a so-called IV administration set including, for example, a bottle of fluid to be administered and typically positioned upside down, a sterile plastic tubing set, and a pump for pumping fluid from the bottle through the IV set to the patient. Other mechanisms may be included to manually stop the flow of fluid to the IV feeding tube and possibly some monitoring devices.

Current IV pumps generally are of two basic types: electronic pumps and disposable non-electronic pumps. Although the electronic pumps have been significantly miniaturized and do include some disposable components, they are nevertheless generally high in cost, require frequent maintenance with continued use, and may be difficult for a layman to operate if, for example, self treatment is desired.

The disposable non-electric pumps generally consist of small elastomeric bags within a hard shell container, in which the bags are filled with IV solution under pressure. The pressure generated by the contraction of the elastomeric bag forces the IV solution through a fixed orifice at a constant flow rate into the patient's vein. Although these pumps are much less expensive than the electronic pumps and eliminate the need for maintenance (since they are discarded after every use), their drawbacks include the lack of monitoring capability, the lack of the ability to select different flow rates, limited fluid capacity, and still relatively high cost for a disposable product.

It is often desirable to accomplish fluid delivery by a topical administration of the fluid to allow the fluid to drift into the skin by osmosis. The HARTS COLLAR™ is known in the art to include a porous fluid holder for strapping around the neck of a patient, usually a dog. The porosity of the collar is designed to release the contained fluid from the collar at a desirable rate onto the skin of the patient to enable the skin to gradually absorb the fluid. The drawbacks include nonuniform application due to movement of the patient, nonuniform delivery rates, and the lack of ability to select different flow rates.

OBJECTS AND SUMMARY OF THE INVENTION

It is therefore an object of the present invention to provide a fluid delivery system which is especially suitable for use in topical administration of fluids to a patient, either human or animal.

It is another object of the invention to provide such a fluid delivery system which utilizes a pump structure to pump multiple fluid doses of predetermined volume to the patient.

It is a further object of the invention to provide such a fluid delivery system which is easy to manufacture and which utilizes low cost parts.

It is an additional object of the invention to provide such a fluid delivery system which is efficient and reliable.

It is another object of the invention, in accordance with one aspect thereof, to provide such a fluid delivery system having a pump structure which is configured to sweep bubbles from a pumping chamber during operation.

It is still another object of the invention, in accordance with one aspect thereof, to provide such a fluid delivery system having a readily changeable flow rate.

It is yet another object of the invention, in accordance with one aspect thereof, to provide such a fluid delivery system which is portable and miniaturized so as to be carryable by the patient.

It is an additional object of the invention, in accordance with one aspect thereof, to provide such a fluid delivery system which delivers doses of fluid to the patient according to a timed sequence.

The above objects and others not specifically recited are realized in a specific illustrative embodiment of pumping apparatus in combination with valved guide channels. A piston-actuated pump utilizes a simple circumferential polymeric seal, or sphincter seal, to retain and prevent loss or leaking of the fluid being pumped. A housing defines an elongate cavity with an opening formed in a first side of the housing, and an opposing second side of the housing is closed. A resilient sheet of material is disposed over the opening in the housing, with the sheet including an aperture positioned in alignment with the cavity at the first side. An elongate shaft is slidably disposed in the aperture so that one end of the shaft extends into the cavity and the other end extends out of the housing. The aperture has substantially the same cross-sectional shape as that of the shaft, and the same cross-sectional dimensions or smaller. An inlet is provided in the housing, through which fluid from a fluid source may flow into the cavity, and an outlet is also provided in the housing, through which fluid may flow from the cavity to a fluid sink. The resilient sheet of material surrounds and grips the shaft at the aperture in the sheet to provide a sphincter seal which prevents fluid from flowing through the aperture but allows the shaft to slide longitudinally therein.

When the shaft is moved in a direction outwardly of the housing, a negative pressure is produced in the cavity to draw in fluid through the inlet, and when the shaft is moved inwardly into the cavity, a positive pressure is produced in the cavity to force fluid from the cavity through the outlet. Check valves may be provided in or near the inlet and outlet to allow fluid only to flow into the cavity through the inlet and out of the cavity through the outlet.

A variety of driver mechanisms and control methods may be provided to cause the shaft to reciprocate within the cavity to produce the pumping action, including ratchet drives, magnetic linear step motors, rotary-to-linear crank drives, and screw drive mechanisms. A variety of valves using sphincter seals and similar mechanisms may be provided to control fluid flow in the pump, among other mechanisms.

Additional objects and advantages of the invention will be set forth in the description which follows, and in part will be apparent from the description, or may be learned by the practice of the invention. The objects and advantages of the invention may be realized and obtained by means of the instruments and combinations particularly pointed out in the appended claims.

BRIEF DESCRIPTION OF THE DRAWINGS

The above and other objects, features and advantages of the invention will become apparent from a consideration of the subsequent detailed description presented in connection with the accompanying drawings in which:

FIG. 5 is a front view of an embodiment of the fluid delivery pump of FIG. 1;

FIG. 5A is one side view of the fluid delivery pump of FIG. 5; and

FIG. 5B is an adjacent side view of the fluid delivery pump of FIG. 5, with respect to the side view of FIG. 5A.

DETAILED DESCRIPTION

Figure 1A:
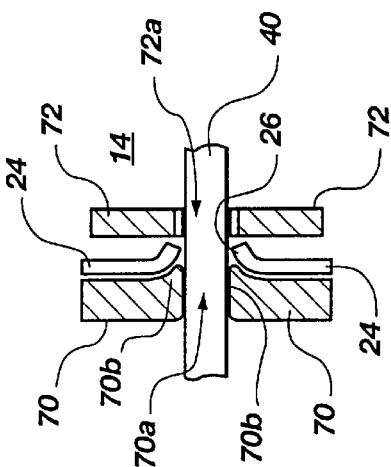
FIG. 1A is a fragmented, side cross-sectional view of a preferred embodiment of front and rear supports of a sphincter seal in the fluid delivery pump of FIG. 1A.
Figure 1:
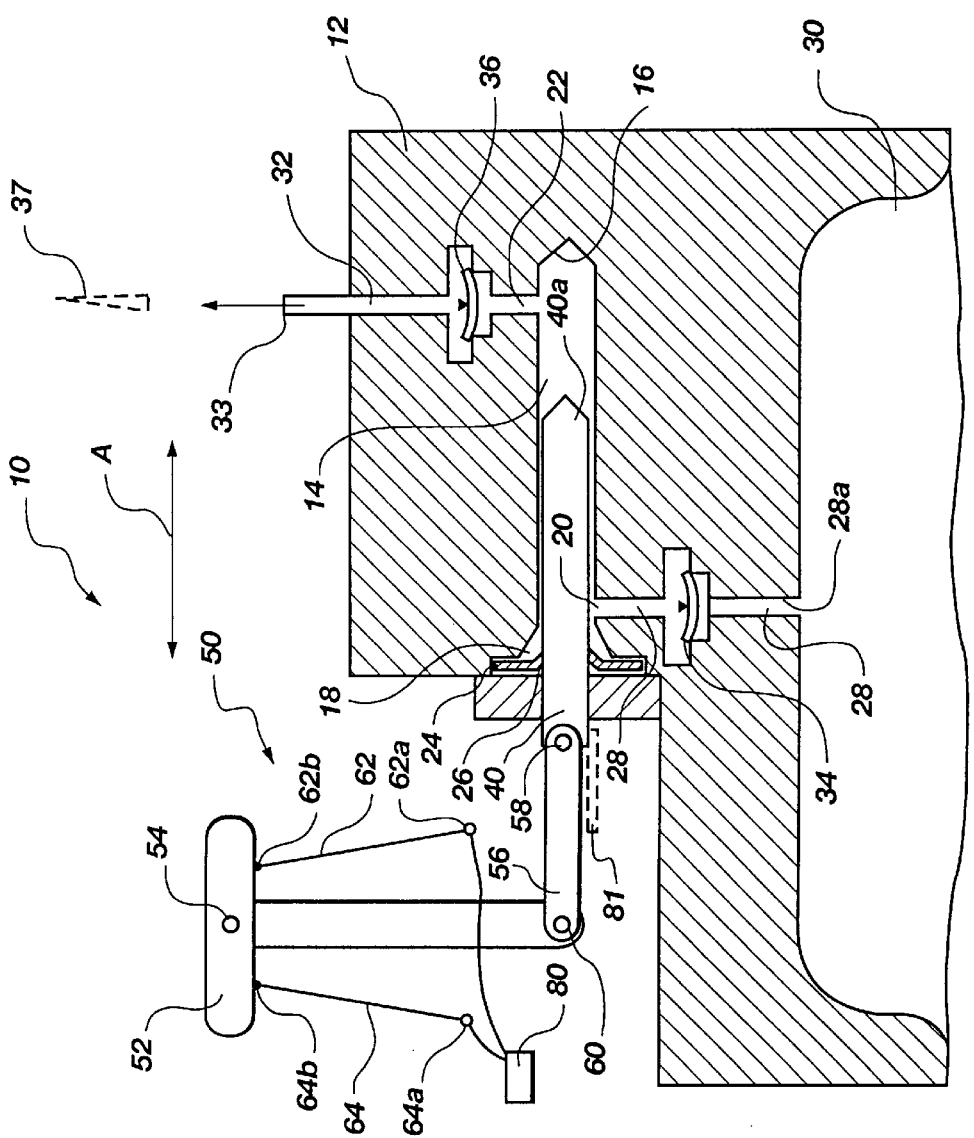
FIG. 1 is a schematic illustration of a piston-actuated fluid delivery pump made in accordance with the principles of the present invention.

Referring to FIG. 1, there is shown a schematic illustration of a piston-actuated pump made in accordance with the present invention, generally designated at 10. The pump 10 includes a housing 12 formed with a generally elongate intermediate dosing chamber 14 therein. The dosing chamber 14 includes a closed end 16, a piston-receiving opening 18 opposite the closed end, and inlet and outlet ports 20 and 22, respectively.

A resilient sheet of material 24 made, for example, of latex rubber, silicone rubber, nitrile rubber or thermoplastic elastomers, is disposed over the piston-receiving opening 18 to sealably close off the opening, except for an aperture 26 formed in the sheet. The sheet of material 24 operates to prevent communication between the outside of the housing 12 and the dosing chamber 14 except through the aperture 26.

An inlet channel 28 provides communication between the inlet port 20 and a fluid reservoir 30. An outlet channel 32 includes a distal end or discharge end 33, and similarly provides communication between the outlet port 22 and the outside of the housing. The channels 28 and 32 may illustratively be conduits disposed within elongate cavities formed in the housing 12. First and second check valves 34 and 36 are disposed respectively in the inlet and outlet channels 28 and 32. Check valves are passive valves known in the art for allowing fluid to flow within a channel in one direction but not in a reverse direction. Thus, the first check valve 34 permits fluid to flow from the reservoir 30 into the dosing chamber 14, but not from the dosing chamber into the reservoir. Similarly, the second check valve 36 permits fluid to flow from the dosing chamber 14 to the discharge end 33 of the outlet channel 32, but not in the reverse direction. Of course, the check valves 34 and 36 may be replaced with other valves suitable for allowing fluid flow in one direction and preventing reverse flow in an opposing direction. For example, properly timed active valves which open and close during appropriate intervals of the pumping cycle of the pump 10 could replace the check valves 34 and 36.

An elongate piston 40 is slidably disposed in the aperture 26 of the sheet of material 24 to extend at least partially into the dosing chamber 14. The piston 40 preferably has a circular cross section and a somewhat smaller circumference than that of the dosing chamber 14 so that the piston may be moved in a reciprocating fashion back and forth in the aperture 26 and chamber 14. The aperture 26 is preferably shaped similarly to the cross-sectional shape of the piston 40 and is preferably the same or slightly smaller in size in order to completely surround and grip the piston to form a sphincter seal and prevent fluid from escaping the chamber 14. Since the sheet of material 24 is resilient, the aperture 26 conforms to the shape of the piston 40 even if their respective shapes are not identical.

A suitable driving mechanism, generally designated at 50, operates to move the piston 40 back and forth in the directions shown by arrow A in a reciprocating motion. A preferred driving mechanism 50 includes a T-shaped shaft 52 pivotally mounted at pin 54. A shaft link member 56 is attached at one end to the piston 40 and at an opposing end to the T-shaped shaft 52, by connections 58 and 60, respectively. The connections 58 and 60 are preferably pivotal connections. Shape memory wires 62 and 64 are rigidly attached at one end to support structure at 62a and 64a, respectively. The wires 62 and 64 are rigidly attached at their opposing ends to opposing portions of the T-end of the T-shaped shaft 52 at 62b and 64b, respectively. A source of electricity 80 is connectable to selectively pass electrical current through said shape memory wires. The operation of the driving mechanism 50 will be discussed in more detail below.

In operation, the driving mechanism 50 moves the piston 40 back and forth in the directions of arrow A as discussed above between first and second positions. A negative pressure is produced within the dosing chamber 14 when the piston 40 is pulled out of the chamber to a first position, and a positive pressure is produced when the piston is pushed into the chamber to a second position. The positive pressure forces any fluid residing in the chamber through the outlet port 22 into the outlet channel 32 and through the second check valve 36 to the discharge end 33 of the outlet channel. When the piston 40 is caused to retract outwardly from the dosing chamber 14, the resulting negative pressure causes fluid to be drawn from the reservoir 30 through the first check valve 34 and inlet port 20 into the dosing chamber 14. The continued reciprocating motion of the piston 40 thereby provides for pumping fluids from the reservoir 30 to the discharge end 33 of the outlet channel 32.

The distal end 33 of the outlet channel 32 delivers the fluid pumped from the reservoir 30. The distal end is placed proximate to the desired point of delivery of the fluid. If topical delivery is desired, the distal end 33 may be placed against a portion of the skin which is to absorb the fluid. Alternatively, an intravenous needle 37 (shown in phantom line in FIG. 1) may be attached to the distal end 33 for intravenous application of the fluid pumped from the reservoir 30.

One advantage to the pump shown in FIG. 1 is that the corresponding shapes of the piston 40 and dosing chamber 14 cause gas bubbles to be swept out of the chamber with each stroke of the piston, instead of accumulating in the chamber, especially around the seal made in the sheet 24. This allows for greater volumetric accuracy in the pumping action, in that prevention of bubbles provides delivery of the correct dosage of fluid.

FIG. 1A shows a fragmented, side, cross-sectional view of the piston 40, the aperture 26 in the resilient sheet 24, with the addition of forward and rear seal supports 70 and 72. The supports 70 and 72 allow for greater positive or negative fluid pressure in the dosing chamber 14 by supporting the sheet 24 at the aperture 26 so that it does not distend with the movement of the piston 40 into the chamber (to thus stretch and degrade the resilient material and damage the seal), or collapse with the movement of the piston 40 out of the chamber (to further degrade the material and damage the seal). Greater fluid pressure in the chamber exacerbates the problems of distending and collapsing the sheet 24, which the supports 70 and 72 help prevent.

The rear support 72 preferably comprises an inflexible flat plate with an aperture 72a formed therein. The aperture 72a is preferably similar in shape and slightly larger in size than the piston 40 to allow free movement of the piston therein, and is located close to the sheet 24. During movement of the piston 40 into the dosing chamber 14, the friction of the piston 40 against the sheet 24 at the aperture 26 tends to cause the latter to distend toward the chamber 14. The sheet 24 at the aperture 26, however, contacts the support 72 before distending enough to damage the material or loosen the seal.

Like the rear support 72, the forward support 70 preferably comprises a plate with an aperture 70a formed therein, but also a lip 70b around the aperture, extending toward the dosing chamber 14. The lip 70b is preferably shaped to approximate the shape of the sheet 24 at the aperture 26 after the piston 40 has been inserted therein. During movement of the piston 40 out of the chamber 14, the fluid pressure in the chamber and the friction of the piston 40 against the sheet 24 at the aperture 26 tend to cause the aperture to collapse upon itself in a direction away from the chamber 14. The forward support 70, however, prevents collapsing and maintains the desired position of the sheet 24 at the aperture 26 during withdrawal of the piston 40 from the chamber 14. The support 70 also bears a large amount of fluid pressure from the chamber 14, relieving somewhat the pressure on the sheet 24.

Those skilled in the art will appreciate the disadvantages associated with "dead volume" or "dead space" in pumping devices. For example, if the piston 40 is much shorter than the elongate dosing chamber 14, the pump 10 will be much less efficient, in part because a "dead space" will remain between a distal end 40a of the piston 40 and closed end 16 of the chamber. The fluid residing in the dead space during pumping action must absorb the pressures involved and may develop air spaces therein. For these and other reasons known to those skilled in the art, a dead space may result in inaccurate and/or inconsistent dosages pumped from the pump 10. Therefore, the shape of the distal end 40a of the piston 40 preferably corresponds to the shape of the closed end 16 of the dosing chamber 14, and the piston 40 is preferably of a length sufficient to cause the distal end 40a to contact or closely approach the closed end 16.

Further, the inlet port 20 is preferably disposed closely adjacent to the piston-receiving opening 18 of the dosing chamber 14, and the outlet port 22 is preferably disposed closely adjacent to the closed-end 16 of the dosing chamber 14. These structural particulars minimize dead spaces within the dosing chamber 14 by causing substantially all of the fluid withdrawn from the reservoir 30 in a pumping cycle to be advanced to the outlet channel 32 during that same pumping cycle. Applicants have found that bubbles within the fluid being pumped are minimized by provision of the inlet port 20 closely adjacent to the piston-receiving opening 18. The inlet port 20 most preferably resides as close as practical to the piston-receiving opening 18 such as within one-fourth of the chamber length from the opening 18. Similarly, the outlet port 22 most preferably resides as close as practical to the closed-end 16 of the dosing chamber 14 such as within one-fourth of the chamber length from the closed end 16.

It may be desirable to vary the pumping speed of the piston 40 in order to vary the rate fluid of pumped from the reservoir 30. For example, a stop means 81 could be incorporated to stop movement of the piston 40 at selectable distances to thereby change the volume of fluid pumped per stroke.

Figures 2, 2A:
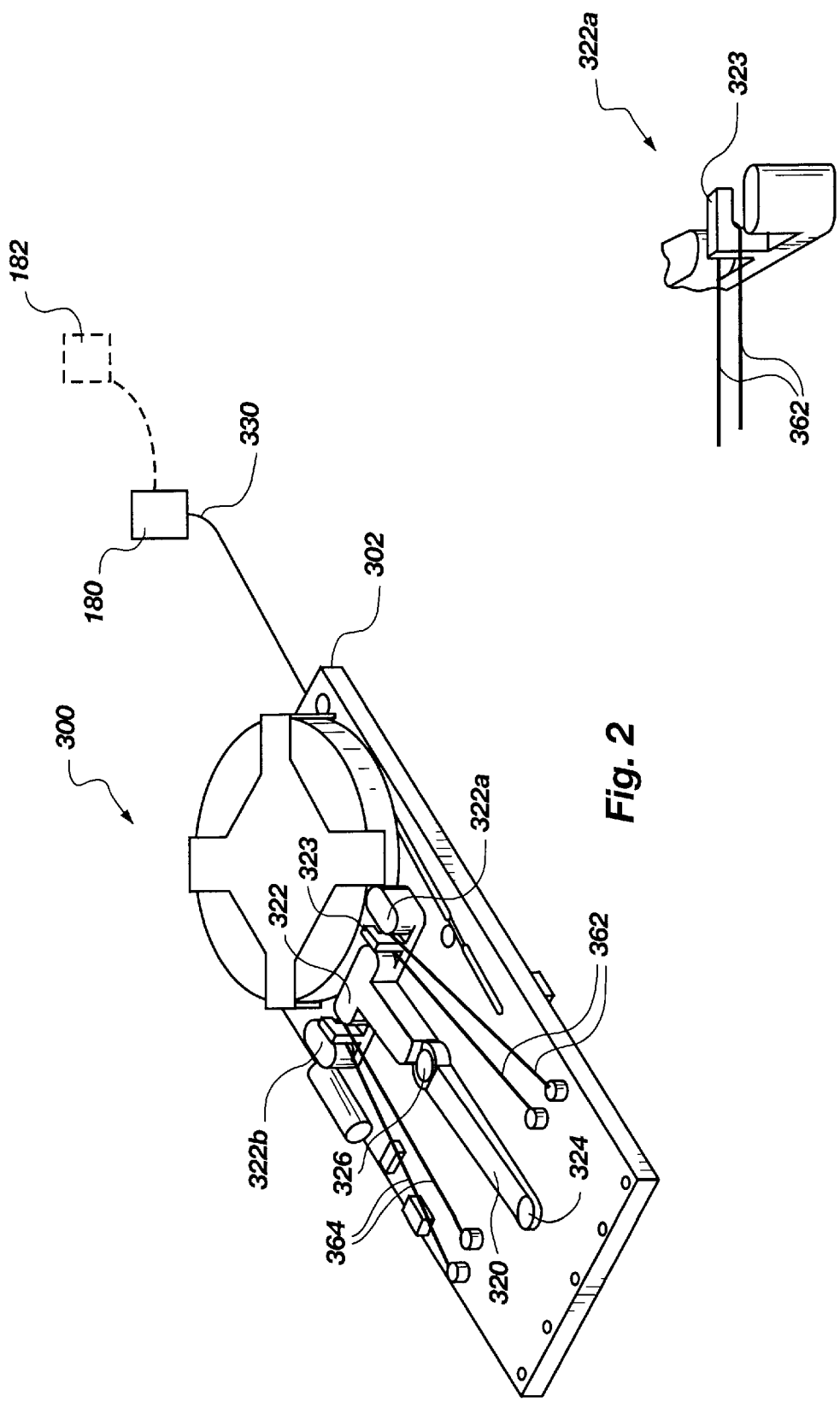
FIG. 2 is a perspective view of a switching device of the fluid delivery pump of FIG. 1.
FIG. 2A is an enlarged view of a first end portion of a shaft body of the switching device of FIG. 2.

The driving mechanism 50 may of course assume many different alternative embodiments. One such embodiment is illustrated in FIGS. 2 and 2A, wherein a shape-memory wired switching device 300 is shown. First shape memory wire 362 and second shape memory wire 364 operate to drive the switching device 300, as explained below in more detail. Shape memory materials are malleable when their temperature is below the material's transition temperature. When heated above the transition temperature, the material forcefully returns to its original shape. One method of heating a wire is to pass electric current through it.

The switching device 300 includes a support plate 302. A rigid shaft body 320 includes first and second opposing ends 322 and 324, and is pivotally mounted to the support plate 302 at a pivot point 326 thereof. The first opposing end 322 has first and second opposing sides 322a and 322b.

The first shape memory wire 362 is secured at one end thereof to the support plate 302 and attached at an opposing end thereof to the first side 322a of the first end 322 of the shaft body 320. The second shape memory wire 364 is secured at one end thereof to the support plate 302 and attached at an opposing end thereof to the second side 322b of the first end of the shaft body. As shown most clearly in FIG. 2A, each shape wire is preferably looped around a finger 323 formed on a side of the first end 322 of the shaft body 320. For example, the first shape wire 362 is wrapped around a finger 323 of the first side 322a for a secure attachment thereto. The term "attachment" as used herein with respect to shape memory wires shall thus refer broadly to stationary attachment and looped attachment, as well as any other suitable attachment.

Current means 330 for alternately passing electrical current through the first and second shape memory wires 362 and 364 is electrically connected to said shape memory wires. The current means 330 is electrically connected to a source of electricity 180. The current means 330 is operable in any manner known in the art to alternately cause the first shape memory wire 362 and the second shape memory wire 364 to contract in alternating tandem. Contraction of the first shape memory wire 362 causes the shaft body 320 to pivot about its pivot point 326 in one pivotal direction, and contraction of the second shape memory wire 364 causes the shaft body to pivot about the pivot point in a second pivotal direction.

It will be appreciated by inspection of FIG. 2 that the alternating contraction and release of the first and second shape memory wires 362 and 364 operate to move the second end 324 of the shaft body 320 between at least first and second positions. The second end 324 of the shaft body 320 can be coupled to the piston 40 to incorporate the switching device 300 into the pump 10 of FIG. 1. It is preferable to intercouple the second end 324 to the piston 40 with the link member 56 and pivotal connections 58 and 60, to enable pivotal movement of the shaft body 320 to cause a generally linear reciprocating movement of the piston 40 between first and second positions.

It may be desirable to vary the switching rate of the switching device 300. Electronic control means 182 could be electrically connected to the electricity source 180, to control the flow of electricity therefrom, for example by intermittently stopping and releasing electron flow from the electricity source 180.

Figure 4:
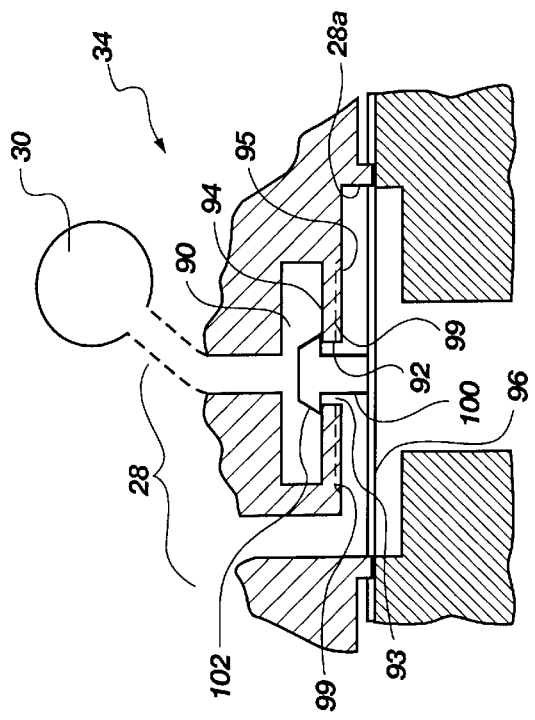
FIG. 4 is a schematic view of anti-blow-through valve of the fluid delivery pump of FIG. 1.
Figure 3A:
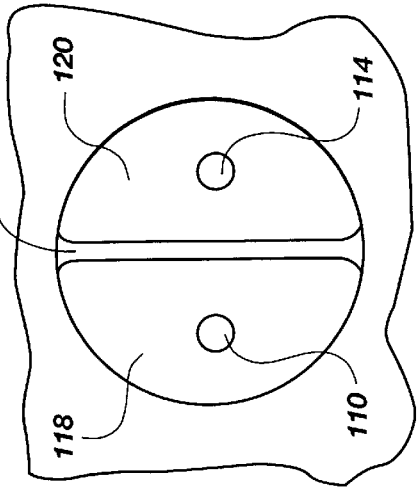
FIG. 3A is a cross-sectional view of the valve of FIG. 3, taken along section A—A.
Figure 3:
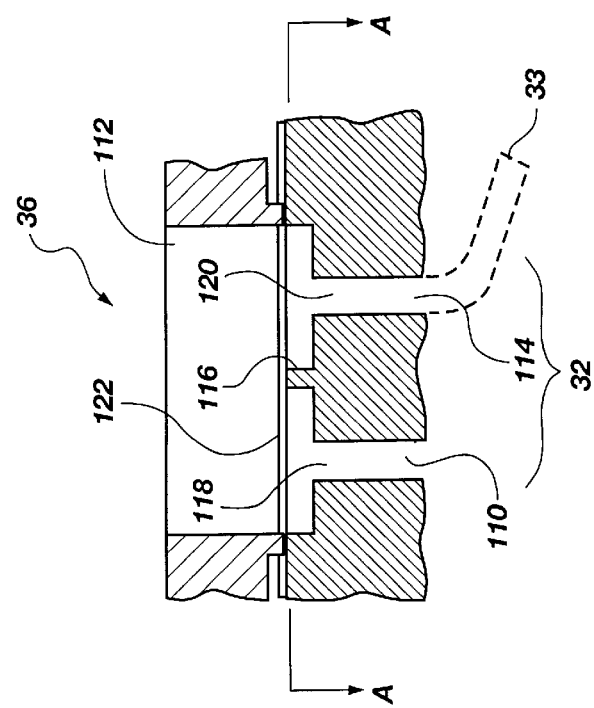
FIG. 3 is a schematic view of an accumulator/anti-suction valve of the fluid delivery pump of FIG. 1.

Preferred embodiments of the first and second check valve 34 and 36 are shown in FIGS. 4 and 3, respectively. The inlet channel 28 includes conduit side walls 28a for conveying fluid from the fluid reservoir 30 to the dosing chamber 14, and the first valve 34 is disposed within the inlet channel to operate as an anti-blow-through valve. Referring now to FIG. 4, the inlet channel 28 and the first valve 34 collectively include an enlarged valve chamber 90 having a valve-head seating brim 92, said brim defining a valve port 93 and having an inlet side 94 and an opposing outlet side 95. A resilient membrane 96 is anchored to the conduit side walls 28a so as to face the outlet side 95 of the brim 92. A neck member 100 is anchored at one end to the resilient membrane 96 and includes an opposing end extending into the valve port 93. The neck member 100 is narrower at said opposing end than the valve port 93 so as to permit fluid flow through the valve port. A valve head 102 is wider than the valve port 93 and is anchored to the opposing end of the neck member 100 so as to reside within the enlarged valve chamber 90. The valve head 102 is seated against the inlet side 94 of the brim 92 so as to cover the valve port 93 in a natural biased position.

The valve head 102 is sufficiently wide so as to prevent passage thereof through the valve port 93, and the resilient membrane 96 is configured and positioned so as to be expandable toward the outlet side 95 of the brim 92 such that (i) positive pressure within the inlet channel 28 operates to force the valve head 102 against the inlet side 94 of the brim 92 to thereby seal the valve head against the brim and block fluid flow within the inlet channel through the valve port 93, and (ii) negative pressure within the inlet channel 28 operates to stretch the resilient membrane 96 toward the outlet side 95 of the brim 92 to thereby move the valve head 102 away from the brim and permit fluid flow within the inlet channel 28 through the valve port 93. It will be appreciated that the valve 34 thus prevents unwanted flow rates due to inadvertent or unwanted pressure upon the fluid reservoir 34. For example, if someone were to carelessly squeeze the reservoir 34, the valve 34 would prevent a corresponding spurt of the fluid out through the outlet channel 32.

The brim 92 preferably includes at least one groove 99 formed therein in the outlet side 95, and most preferably a plurality of such grooves 99 (shown in phantom line in FIG. 4). The grooves 99 communicate with the valve port 93 and extend from the valve port radially outward therefrom along the outlet side 95 of the brim 92 a sufficient distance so as to maintain fluid flow through the valve port 93 when the resilient membrane 96 is moved into contact with the outlet side of the brim. Thus, if the piston 30 produces enough suction within the inlet channel 28 to pull the membrane 96 up against the brim 92, the grooves 99 would operate to maintain fluid flow through the valve port 93 and thereby prevent the membrane 96 from unduly obstructing the fluid flow within the inlet channel 28.

Referring now to FIGS. 3 and 3A, the outlet channel 32 and the second valve 36 collectively include an inlet passage 110, an enlarged accumulation chamber 112, and an outlet passage 114 in communication with the distal end 33. An interior side of the accumulation chamber 112 comprises a membrane-seating surface 116 having first and second openings 118 and 120, respectively, formed therein. The inlet and outlet passages 110 and 114 are disposed in communication with the accumulation chamber 112 via the first and second openings 118 and 120, respectively, such that the inlet passage, accumulation chamber and outlet passage respectively reside in series. A second resilient membrane 122 is anchored within the accumulation chamber 112 and is seated against the membrane-seating surface 116 so as to cover the first and second openings 118 and 120 in a natural biased position.

The second resilient membrane 122 is configured and positioned so as to be expandable away from the first and second openings 118 and 120 into the accumulation chamber 112 such that (i) negative pressure within either the inlet passage 110 or the outlet passage 114 operates to pull the membrane 122 toward the membrane-seating surface 116 in sealing contact therewith to thereby block fluid flow within the outlet channel 32, and (ii) positive pressure within either the inlet passage 110 or the outlet passage 114 operates to force the resilient membrane 122 away from the membrane-seating surface 116 to thereby permit fluid to forcibly expand the membrane into the accumulation chamber 112 and thus accumulate within the accumulation chamber and flow within the outlet channel 32 through the first and second openings 118 and 120.

The anti-suction feature of the second valve 36 thereby prevents unwanted suction from inducing fluid flow. For example, a child sucking upon the distal end 33 of the outlet channel 32 is prevented from ingesting the fluid stored in the fluid reservoir 30, which might illustratively comprise morphine. The accumulation feature provided by the accumulation chamber 112 in combination with the second resilient membrane 122 has a number of advantages. For example, friction against fluid flow with the outlet channel may require several hundred pounds per square inch (psi) of pressure to be exerted by the driving mechanism 50 (or switching device 300), especially for more viscous fluids. However, the invention can be designed such that required doses of the fluid require only intermittent pumping cycles, for example, one pumping cycle per 15-minute interval. A sufficiently flexible second membrane 122 (such as can be readily made from latex rubber, silicone rubber, nitrile rubber, or thermoplastic elastomers), however, might illustratively require only a few psi of pressure for the fluid to expand it and fill the accumulation chamber 112. The pump 10 could pump one pumping cycle to fill the accumulation chamber at much lower power since only a few psi of pressure is required. Thereafter, elastic memory of the second membrane 122 would operate to slowly force the fluid residing in the accumulation chamber 112 through the outlet passage 114 and distal end 33 of the outlet channel 32, over the 15-minute interval, for example. The pump 10 would then refill the accumulation chamber 112 within another single pumping cycle, and the process would repeat itself.

Referring now to FIGS. 5, 5A and 5B, the fluid pump 10 can be designed to fit compactly within a steel case 200. Power for energizing the pump 10 can be derived by provision of batteries 202 and 204, which might illustratively comprise an AAAA battery and an A76 alkaline button cell, respectively, as known in the art. The reservoir 30 preferably includes interior side walls having a rigid portion 230 and a freely moveable flexible portion 232. The freely moveable flexible portion 232 of the side walls is moveable into contiguous contact against the rigid portion 230 to thereby substantially eliminate free space within the reservoir means. The flexible portion 232 is preferably vacuum formed as known in the art to conformably and contiguously rest against the rigid portion 230 after all, or substantially all, of the fluid residing in the reservoir 30 has been pumped therefrom. This prevents the pump 10 from storing unwanted residual fluid.

One advantage of the present invention is portability. It will be appreciated by those skilled in the art that the pump 10 of FIG. 1 may be readily constructed from lightweight materials in relatively small dimension. Referring now to FIG. 5B, one application envisioned for the present invention is to incorporate the fluid pump 10 into a collar device 210. The collar device 210 can be strapped around the neck of a dog to deliver doses of fluid as a desired rate, such as anti-tick solution, anti-flea solution, anti-heartworm solution, and so forth. Accordingly, the term "patient" as used herein with respect to application of the invention shall refer broadly to both humans and animals. The collar device 210 enables attachment of the pump 10 to the patient to thereby enable the pump to be carried by the patient in a convenient manner.

In another application envisioned for the invention, the pump 10 is dimensioned and sized so as to be swallowable by the patient to thereby enable the pump to deliver fluid within an intracorporeal region of the patient. For example, a pump in accordance with the invention could contain a supply of anti-parasitic solution useful to prevent parasites on cows. After the cow swallows the miniature pump, it comes to reside in the cow's rumen (the first of the cow's stomachs) and delivers the solution directly into the cow where the solution is advantageously absorbed by the cow. Thus, the phrase "configured for attachment to the patient" as used herein with respect to the invention shall refer broadly to a pumping device which can be strapped to a part of a patient, and/or which can be swallowed by the patient.

It will be appreciated that the invention may include a control means 180 (in FIG. 2) electrically connected to the switching device 300. The control means 180 may include a timer as known in the art for producing timing signals. It will be appreciated that the driving mechanism can be designed to be activated and/or deactivated responsive to the timing signals produces by the timer of the control means. The control means could alternatively include sensing means responsive to some physiological condition of the patient. When the physiological condition of the patient, such as the patient's temperature, reaches a predetermined level, the sensing means would produce an actuation signal to cause the control means to activate and/or deactivate the driving mechanism. The phrase "physiological condition" as used herein shall refer broadly to any function or activity of living organisms and their parts.

Those skilled in the art will appreciate that the scope of the present invention encompasses many combinations and a broad spectrum of features and structures equivalent to those specifically discussed herein. The principles of the invention may thus be used in any setting requiring the advantages thereof. Those having ordinary skill in the field of this invention will appreciate the advantages of the invention and its application to a wide variety of uses. The present invention represents a significant advance in the field of fluid delivery. Those skilled in the art will appreciate from the preceding disclosure that the objectives stated above are advantageously achieved by the present invention.

It is to be understood that the above-described arrangements are only illustrative of the application of the principles of the present invention. Numerous modifications and alternative arrangements may be devised by those skilled in the art without departing from the spirit and scope of the present invention and the appended claims are intended to cover such modifications and arrangements.

What is claimed is:

1. A fluid delivery device for delivering fluid to a patient comprising:

inlet means configured for placement in fluid communication with a fluid reservoir containing a supply of the fluid;

outlet means disposed in fluid communication with the inlet means such that said inlet and outlet means reside in series;

a housing defining an intermediate dosing chamber therein disposed between and in fluid communication with the inlet means and the outlet means, said housing including a piston receiving opening in communication with the chamber;

a resilient sheet of material disposed over the piston receiving opening and including an aperture positioned in alignment with said opening, wherein cross-sectional dimensions of the aperture do not exceed cross-sectional dimensions of the chamber;

an elongate piston slidably disposed in the aperture of the resilient sheet so that one end of the piston extends into the chamber;

shaft means coupled to a proximal end of the piston;

first and second shape memory means attached to opposing portions of the shaft means, said first shape memory means being operable to move the piston to the first position when said first shape memory means is caused to contract, and said second shape memory means being operable to move the piston to the second position when said second shape memory means is caused to contract; and means for alternately passing electrical current through the first and second shape memory means to thereby alternately cause the first shape memory means and the second shape memory means to contract in alternating tandem, so as to cause said piston to slide back and forth through the aperture in a reciprocating motion between first and second positions to pump fluid from the reservoir through the outlet means and to the patient by alternately producing a negative and a positive pressure within the chamber.

2. A fluid delivery device as defined in claim 1, further comprising:

support means, said shaft means being pivotally mounted to the support means at a pivot point;

said shaft means further comprising first and second opposing ends, said first end having first and second opposing sides, and said shaft means being coupled at the second end thereof to the piston;

the first shape memory means being secured at one end thereof to the support means and attached at an opposing end thereof to the first side of the first end of the shaft means;

the second shape memory means being secured at one end thereof to the support means and attached at an opposing end thereof to the second side of the first end of the shaft means; and wherein the means for alternately passing electrical current through the first and second shape memory means to thereby cause the first and second shape memory means to contract in alternating tandem mobilizes the shaft means in reciprocating pivotal movement, such that contraction of the first shape memory means causes pivotal movement of the shaft means and linear movement of the piston into the first position, and contraction of the second shape memory means causes pivotal movement of the shaft means and linear movement of the piston into the second position.

3. A fluid delivery device as defined in claim 2, further comprising a linkage member pivotally attached to the second end of the shaft means and also pivotally attached to the piston so as to intercouple said shaft means and piston to thereby enable the pivotal movement of the shaft means to cause a generally linear reciprocating movement of the piston between first and second positions.

4. A fluid delivery device as defined in claim 2, wherein each of the first and second opposing sides of the first opposing end of the shaft means includes a finger member formed thereon, and wherein the attachment of the first and second shape memory means to said first and second opposing sides, respectively, comprises said first and second shape memory means being looped around the finger member of said first and second opposing sides, respectively.

5. A fluid delivery device as defined in claim 1 further comprising support means on each side of the resilient sheet of material adjacent the aperture for contacting and preventing distending and collapsing of the sheet of material as the piston slides through the aperture.

6. A fluid delivery device as defined in claim 1 wherein the resilient sheet of material is a material selected from the group consisting of latex rubber, silicone rubber, nitrile rubber, and thermoplastic elastomers.

7. A fluid delivery device as defined in claim 1, wherein the inlet port resides within one-fourth of the chamber length from the piston-receiving opening of the housing, and wherein the outlet port resides within one-fourth of the chamber length from the second end of the chamber.

8. A fluid delivery device as defined in claim 1 wherein cross-sectional dimensions of the aperture do not exceed cross-sectional dimensions of the piston.

9. A fluid delivery device as defined in claim 1, wherein said inlet means includes:

a first conduit for conveying fluid from a fluid reservoir to the dosing chamber, and first check valve means disposed in the first conduit for allowing the fluid to flow from the fluid reservoir to the dosing chamber, and for preventing the fluid from flowing from the dosing chamber to the fluid reservoir, and wherein said outlet means includes a second conduit having a distal end for carrying fluid from the dosing chamber to said distal end, and second check valve means disposed in the second conduit for allowing the fluid to flow from the dosing chamber through the distal end of the second conduit, and for preventing the fluid from flowing from the distal end of the second conduit to the dosing chamber.

10. A fluid delivery device as defined in claim 1, wherein said inlet means includes:

a first conduit having conduit side walls for conveying fluid from a fluid reservoir to the dosing chamber, and normally closed first valve means disposed in the first conduit for (i) preventing fluid flow within said first conduit responsive to positive pressure, and (ii) permitting fluid flow within said first conduit responsive to negative pressure.

11. A fluid delivery device as defined in claim 10, wherein the first conduit and the first valve means collectively comprise:

an enlarged valve chamber having a valve-head seating brim, said brim defining a valve port and having an inlet side and an opposing outlet side;

a resilient membrane anchored to the conduit side walls so as to face the outlet side of the brim;

a neck member anchored at one end to the resilient membrane and including an opposing end extending into the valve port, said neck member being narrower at said opposing end than the valve port so as to permit fluid flow through said valve port;

a valve head being wider than the valve port and anchored to the opposing end of the neck member so as to reside within the enlarged valve chamber, said valve head being seated against the inlet side of the brim so as to cover the valve port in a natural biased position.

12. A fluid delivery device as defined in claim 11, the valve head being sufficiently wide so as to prevent passage thereof through the valve port and wherein the resilient membrane is configured and positioned so as to be expandable toward the outlet side of the brim such that (i) positive pressure within the first conduit operates to force the valve head against the inlet side of the brim to thereby seal said valve head against the brim and block fluid flow within the first conduit through the valve port, and (ii) negative pressure within the first conduit operates to stretch the resilient membrane toward the outlet side of the brim to thereby move the valve head away from the brim and permit fluid flow within the first conduit through the valve port.

13. A fluid delivery device as defined in claim 11, wherein the outlet side of the brim includes at least one groove formed therein which communicates with the valve port and extends from the valve port radially outward therefrom along said outlet side of the brim a sufficient distance so as to maintain fluid flow through the valve port when the resilient membrane is moved into contact with said outlet side of said brim.

14. A fluid delivery device as defined in claim 1, wherein said outlet means includes:

a second conduit having a distal end for carrying fluid from the dosing chamber to said distal end, and normally closed second valve means disposed in the second conduit for (i) preventing fluid flow within said second conduit responsive to negative pressure, and (ii) permitting fluid flow within said second conduit responsive to positive pressure.

15. A fluid delivery device as defined in claim 14, wherein the second conduit and the second valve means collectively comprise:

an inlet passage, an enlarged accumulation chamber, and an outlet passage, wherein an interior side of the accumulation chamber comprises a membrane-seating surface having first and second openings formed therein, the inlet and outlet passages being disposed in communication with the accumulation chamber via the first and second openings, respectively, such that the inlet passage, accumulation chamber and outlet passage respectively reside in series;

a resilient membrane anchored within the accumulation chamber and being seated against the membrane-seating surface so as to cover the first and second openings in a natural biased position.

16. A fluid delivery device as defined in claim 15, wherein the resilient membrane is configured and positioned so as to be expandable away from the first and second openings and into the accumulation chamber such that (i) negative pressure within either the inlet passage or the outlet passage operates to pull the membrane toward the membrane-seating surface in sealing contact therewith to thereby block fluid flow within the second conduit, and (ii) positive pressure within either the inlet passage or the outlet passage operates to force the resilient membrane away from the membrane-seating surface to thereby permit fluid to forcibly expand the membrane and accumulate within the accumulation chamber and flow within the second conduit through the first and second openings.

17. A fluid delivery device as defined in claim 1 further comprising frequency varying means connected to the actuation means for selectively varying the frequency of reciprocating motion of the piston to thereby vary the rate of pumping of the fluid.

18. A fluid delivery device as defined in claim 17 wherein said actuation means includes:
  pushing means for alternately pushing the piston in a direction into the dosing chamber, and releasing the piston from being pushed, and
  biasing means for forcing the piston in a direction out of the dosing chamber when the piston is released by the pushing means,
  wherein said frequency varying means includes stop means for stopping the movement of the piston in the direction out of the dosing chamber at selectable distances.

19. A fluid delivery device as defined in claim 1, wherein the outlet means includes a distal end portion configured for attachment to an intravenous needle to thereby permit the fluid delivery device to deliver fluid into a vein of the patient.

20. A fluid delivery device as defined in claim 1 wherein said device is portable and miniaturized and configured for attachment to the patient to thereby enable the device to be carried by the patient, such that movement of the device is confined to movement with the patient.

21. A fluid delivery device as defined in claim 20 wherein said device is dimensioned and sized to be swallowable by the patient to thereby enable said device to deliver fluid within an intracorporeal region of the patient.

22. A fluid delivery device as defined in claim 20 further including attachment means for attaching the device to an exterior portion of the patient to thereby enable the device to deliver the fluid to the patient in a topical manner.

23. A fluid delivery device as defined in claim 1 further comprising control means including timing means, said control means being connected to the actuation means for activating and deactivating the actuation means responsive to a timing signal produced by the timing means.

24. A fluid delivery device as defined in claim 1 further comprising control means including sensing means responsive to physiological conditions of the patient, said control means being connected to the actuation means for activating and deactivating the actuation means responsive to an actuation signal produced by the sensing means.

25. A fluid delivery device as defined in claim 1, wherein said inlet means comprises:
  a first conduit having conduit side walls for conveying fluid from a fluid reservoir to the dosing chamber, and first valve means disposed within said first conduit, said first conduit and first valve means collectively comprising:
    an enlarged valve chamber having a valve-head seating brim, said brim defining a valve port and having an inlet side and an opposing outlet side;
    a resilient membrane anchored to the conduit side walls so as to face the outlet side of the brim;
    a neck member anchored at one end to the resilient membrane and including an opposing end extending into the valve port, said neck member being narrower at said opposing end than the valve port so as to permit fluid flow through said valve port;
    a valve head being wider than the valve port and anchored to the opposing end of the neck member so as to reside within the enlarged valve chamber, said valve head being seated against the inlet side of the brim so as to cover the valve port in a natural biased position;
  wherein the outlet means comprises:
    a second conduit having a distal end for carrying fluid from the dosing chamber to said distal end, and second valve means disposed within the second conduit, said second conduit and second valve means collectively comprising:
      an inlet passage, an enlarged accumulation chamber, and an outlet passage, wherein an interior side of the accumulation chamber comprises a membrane-seating surface having first and second openings formed therein, the inlet and outlet passages being disposed in communication with the accumulation chamber via the first and second openings, respectively, such that the inlet passage, accumulation chamber and outlet passage respectively reside in series; and
      a resilient membrane anchored within the accumulation chamber and being seated against the membrane-seating surface so as to cover the first and second openings in a natural biased position.

26. A fluid delivery device as defined in claim 25, the valve head being sufficiently wide so as to prevent passage thereof through the valve port and wherein the resilient membrane is configured and positioned so as to be expandable toward the outlet side of the brim such that (i) positive pressure within the first conduit operates to force the valve head against the inlet side of the brim to thereby seal said valve head against the brim and block fluid flow within the first conduit through the valve port, and (ii) negative pressure within the first conduit operates to stretch the resilient membrane toward the outlet side of the brim to thereby move the valve head away from the brim and permit fluid flow within the first conduit through the valve port.

27. A fluid delivery device as defined in claim 25, wherein the resilient membrane is configured and positioned so as to be expandable away from the first and second openings and into the accumulation chamber such that (i) negative pressure within either the inlet passage or the outlet passage operates to pull the membrane toward the membrane-seating surface in sealing contact therewith to thereby block fluid flow within the second conduit, and (ii) positive pressure within either the inlet passage or the outlet passage operates to force the resilient membrane away from the membrane-seating surface to thereby permit fluid to forcibly expand the membrane and accumulate within the accumulation chamber and flow within the second conduit through the first and second openings.

28. A fluid delivery device as defined in claim 1, further comprising reservoir means disposed in communication with the inlet means for containing a supply of the fluid, said reservoir means having interior side walls including a rigid portion and a freely moveable flexible portion, said freely moveable flexible portion of the side walls being moveable into contiguous contact against the rigid portion to thereby substantially eliminate free space within the reservoir means.

29. A fluid delivery device for delivering fluid to a patient comprising:

inlet means configured for placement in fluid communication with a fluid reservoir containing a supply of the fluid;

outlet means disposed in fluid communication with the inlet means such that said inlet and outlet means reside in series;

a housing defining an intermediate dosing chamber therein disposed between and in fluid communication with the inlet means and the outlet means, said housing including a piston-receiving opening in communication with the chamber;

a resilient sheet of material disposed over the piston-receiving opening and including an aperture positioned in alignment with said opening, wherein cross-sectional dimensions of the aperture do not exceed cross-sectional dimensions of the chamber;

an elongate piston slidably disposed in the aperture of the resilient sheet so that one end of the piston extends into the chamber; and actuation means connected to the piston for causing said piston to slide back and forth through the aperture in a reciprocating motion between first and second positions to pump fluid from the reservoir through the outlet means by alternately producing a negative and a positive pressure within the chamber, respectively, such that when the actuation means advances the piston progressively out of the dosing chamber to the first position a negative pressure is produced in the chamber thereby to cause a dose of fluid to flow from the inlet means into the chamber, and when the actuation means advances the piston progressively into the dosing chamber to the second position a positive pressure is produced in the chamber thereby to forcibly eject the dose of fluid through the outlet means to the patient;

wherein said inlet means comprises:

a first conduit having conduit side walls for conveying fluid from a fluid reservoir to the dosing chamber, and first valve means disposed within said first conduit, said first conduit and first valve means collectively comprising:

an enlarged valve chamber having a valve-head seating brim, said brim defining a valve port and having an inlet side and an opposing outlet side;

a resilient membrane anchored to the conduit side walls so as to face the outlet side of the brim;

a neck member anchored at one end to the resilient membrane and including an opposing end extending into the valve port, said neck member being narrower at said opposing end than the valve port so as to permit fluid flow through said valve port;

a valve head being wider than the valve port and anchored to the opposing end of the neck member so as to reside within the enlarged valve chamber, said valve head being seated against the inlet side of the brim so as to cover the valve port in a natural biased position;

wherein the outlet means comprises:

a second conduit having a distal end for carrying fluid from the dosing chamber to said distal end, and second valve means disposed within the second conduit, said second conduit and second valve means collectively comprising:

an inlet passage, an enlarged accumulation chamber, and an outlet passage, wherein an interior side of the accumulation chamber comprises a membrane-seating surface having first and second openings formed therein, the inlet and outlet passages being disposed in communication with the accumulation chamber via the first and second openings, respectively, such that the inlet passage, accumulation chamber and outlet passage respectively reside in series; and a resilient membrane anchored within the accumulation chamber and being seated against the membrane-seating surface so as to cover the first and second openings in a natural biased position;

wherein the actuation means further comprises:

support means;

rigid shaft means having a pivot point and first and second opposing ends, said shaft means being pivotally mounted to the support means at the pivot point, said first end having first and second opposing sides, said shaft means being coupled at the second end thereof to the piston;

first shape memory means secured at one end thereof to the support means and attached at an opposing end thereof to the first side of the first end of the shaft means;

second shape memory means secured at one end thereof to the support means and attached at an opposing end thereof to the second side of the first end of the shaft means;

means for alternately passing electrical current through the first and second shape memory means to thereby cause the first and second shape memory means to contract in alternating tandem so as to mobilize the shaft means in reciprocating pivotal movement, such that contraction of the first shape memory means causes movement of the piston into the first position and contraction of the second shape memory means causes movement of the piston into the second position;

a linkage member pivotally attached to the second end of the shaft means and also pivotally attached to the piston so as to intercouple said shaft means and piston to thereby enable the pivotal movement of the shaft means to cause a generally linear reciprocating movement of the piston between first and second positions;

reservoir means disposed in communication with the inlet means for containing a supply of the fluid, said reservoir means having interior side walls including a rigid portion and a freely moveable flexible portion, said freely moveable flexible portion of the side walls being moveably into continuous contact against the rigid portion to thereby substantially eliminate free space within the reservoir means.

30. A fluid delivery device as defined in claim 29, wherein the intermediate dosing chamber comprises an elongate chamber defined by interior side walls of the housing, said elongate chamber having first and second opposing ends and wherein the piston-receiving opening is formed in said first end, said elongate chamber further including (i) an inlet port formed in said interior side walls of the housing so as to reside near the piston-receiving opening of the housing with respect to the rest of the chamber, and (ii) an outlet port formed in said interior side walls so as to reside near the second end of the chamber with respect to the rest of the chamber, and wherein the inlet means comprises an inlet channel disposed in communication with the dosing chamber through the inlet port, and wherein the outlet means comprises an outlet channel disposed in communication with the dosing chamber through the outlet port; wherein the inlet port resides as close as practical to the piston-receiving opening of the housing, and wherein the outlet port resides as close as practical to the second end of the chamber.

* * * * *